United States Patent
Hassey et al.

(10) Patent No.: US 11,030,874 B2
(45) Date of Patent: Jun. 8, 2021

(54) BATHROOM CLEAN MONITORING IN A HEALTHCARE FACILITY

(71) Applicant: Hill-Rom Services, Inc., Batesville, IN (US)

(72) Inventors: Laura A. Hassey, Raleigh, NC (US); Steven D. Baker, Beaverton, OR (US); Bradley T. Smith, Raleigh, NC (US); Eric D. Agdeppa, Cincinnati, OH (US); Pamela Wells, Hixson, TN (US); Thomas A. Myers, Syracuse, NY (US); Andrew S. Robinson, Durham, NC (US); Kiana M. Dezelon, Batesville, IN (US); John S. Schroder, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 16/821,231

(22) Filed: Mar. 17, 2020

(65) Prior Publication Data
US 2020/0219374 A1    Jul. 9, 2020

Related U.S. Application Data

(63) Continuation of application No. 16/233,413, filed on Dec. 27, 2018, now Pat. No. 10,629,049.

(60) Provisional application No. 62/621,954, filed on Jan. 25, 2018.

(51) Int. Cl.
*G08B 21/04* (2006.01)
*G08B 21/18* (2006.01)
*G16H 40/63* (2018.01)
*G16H 50/20* (2018.01)

(52) U.S. Cl.
CPC ....... *G08B 21/0446* (2013.01); *G08B 21/182* (2013.01); *G16H 40/63* (2018.01); *G16H 50/20* (2018.01)

(58) Field of Classification Search
CPC .. G08B 21/0492; G08B 21/02; G08B 21/182; G16H 40/63; G16H 50/20
See application file for complete search history.

(56) References Cited

U.S. PATENT DOCUMENTS

| 5,182,823 A | 2/1993 | Alsip |
| 5,838,223 A | 11/1998 | Gallant |
| 7,319,386 B2 | 1/2008 | Collins, Jr. et al. |

(Continued)

FOREIGN PATENT DOCUMENTS

| JP | 2013-134544 A | 7/2013 |
| WO | 2017/08335 A1 | 5/2017 |

*Primary Examiner* — Hongmin Fan
(74) *Attorney, Agent, or Firm* — Barnes & Thornburg LLP

(57) ABSTRACT

A patient fall detection system includes a computer and multiple transceivers mounted at fixed locations in a healthcare facility. The transceivers are electronically coupled to the computer. A patient identification tag is worn by a patient and includes a tag transceiver. The high-accuracy locating system monitors a location of the patient ID tag via signals from the tag transceiver to determine whether a patient has entered a bathroom. The computer monitors at least one of an elevation of the patient ID tag in the bathroom, an elevation drop of the patient ID tag in the bathroom, or a time that the patient ID tag has been in the bathroom to determine whether the patient has fallen.

17 Claims, 6 Drawing Sheets

(56) References Cited

U.S. PATENT DOCUMENTS

| | | |
|---|---|---|
| 7,450,024 B2 | 11/2008 | Wildman et al. |
| 7,538,659 B2 | 5/2009 | Ulrich et al. |
| 8,068,051 B1 | 11/2011 | Osterwell |
| 8,115,641 B1 | 2/2012 | Dempseyd |
| 8,384,526 B2 | 2/2013 | Schuman, Sr. et al. |
| 8,773,269 B2 | 7/2014 | Richardson et al. |
| 9,098,993 B2 | 8/2015 | Reed, Jr. |
| 9,959,733 B2 | 5/2018 | Reed, Jr. |
| 9,984,211 B2 | 5/2018 | Hsu |
| 10,226,177 B2 | 3/2019 | Chamberlain |
| 10,629,049 B2 | 4/2020 | Hassey et al. |
| 2005/0278409 A1* | 12/2005 | Kutzik .................. G16H 20/70 709/200 |
| 2008/0084296 A1* | 4/2008 | Kutzik .................. G16H 40/20 340/540 |
| 2008/0221928 A1* | 9/2008 | Garcia .................. G06Q 50/24 705/3 |
| 2009/0212925 A1 | 8/2009 | Schuman, Sr. et al. |
| 2009/0212956 A1 | 8/2009 | Schuman et al. |
| 2009/0217080 A1 | 8/2009 | Ferguson et al. |
| 2009/0322548 A1 | 12/2009 | Gottlieb |
| 2011/0093287 A1* | 4/2011 | Dicks .................... A61B 5/1112 705/2 |
| 2011/0181422 A1* | 7/2011 | Tran ........................ A61B 7/04 340/573.1 |
| 2013/0141233 A1* | 6/2013 | Jacobs .................. G16H 50/20 340/521 |
| 2014/0145848 A1 | 5/2014 | Amir |
| 2015/0269824 A1 | 9/2015 | Zhang |
| 2016/0034731 A1 | 2/2016 | Lin |
| 2016/0324487 A1* | 11/2016 | Guo ........................ A61B 5/0816 |
| 2018/0075725 A1 | 3/2018 | Geng et al. |
| 2018/0174420 A1 | 6/2018 | Clark et al. |
| 2018/0174671 A1* | 6/2018 | Cruz Huertas ........ G16H 15/00 |
| 2019/0228632 A1 | 7/2019 | Hassey et al. |

* cited by examiner

BATHROOM CLEAN MONITORING IN A HEALTHCARE FACILITY

The present application is a continuation of U.S. application Ser. No. 16/233,413, filed Dec. 27, 2018, now U.S. Pat. No. 10,629,049, which claims the benefit, under 35 U.S.C. § 119(e), of U.S. Provisional Application No. 62/621,954, filed Jan. 25, 2018, and each of which is hereby incorporated by reference herein in its entirety.

BACKGROUND

The present disclosure relates to locating systems used in healthcare facilities to track the locations of patients, and more particularly to bathroom monitoring in a healthcare facility.

Patient rooms in health care facilities are generally equipped with a private bathroom for the patient. Patients who are mobile and able to exit their bed may use the bathroom at any time. This may include using the bathroom unassisted. However, some patients may inadvertently fall while in the bathroom. If a patient falls in the bathroom, significant time may pass before a caregiver finds the fallen patient because the bathroom door is typically closed preventing the patient from being seen on the bathroom floor. If a caregiver enters the patient room with the bathroom door closed, the caregiver will not know that the patient fell in the bathroom and, therefore, will not have any idea how long it may have been since the patient fell. The caregiver may decide to leave the patient room and plan to return after a period of time under the assumption the patient will exit the bathroom while the caregiver is away from the patient room.

Some asset tracking tags or badges may include motion sensors such as accelerometers to monitor patient movement. See, for example, U.S. Pat. No. 7,450,024 in this regard. However, including one or more accelerometers in a tracking tag adds to the overall cost and complexity of the tag. Furthermore, if the tag is included as part of a wrist band on a patient, then abrupt movements of the patient's arm may result in a false positive signal being sent indicating the patient has fallen when, in fact, the patient has not fallen but has merely moved their arm downwardly with a quick motion, for example.

Additionally, the patient's use of the bathroom may go unnoticed by housekeeping. That is, if the patient is unattended, housekeeping cannot track how often the patient is using the bathroom. Because sanitation is particularly desirable in a healthcare facility, it would be beneficial for housekeeping to know when the patient's bathroom should be cleaned. Accordingly, there is room for improving the systems and methods of monitoring patient use of bathrooms in a healthcare facility.

SUMMARY

The present disclosure includes one or more of the features recited in the appended claims and/or the following features which, alone or in any combination, may comprise patentable subject matter.

According to the present disclosure, a patient fall detection system may include a computer that may be configured to track a location of a patient in a healthcare facility. The system may further have a plurality of transceivers that may be mounted at fixed locations throughout the healthcare facility and that may be communicatively coupled to the computer. The system also may have a patient identification (ID) tag that may be worn by the patient. The patient ID tag may have a tag transceiver that may be configured to communicate with the plurality of transceivers. The plurality of transceivers and the computer may cooperate to form a high-accuracy locating system that may be operable to determine a location of the patient ID tag in 3-dimensional space without the use of any accelerometer. The high-accuracy locating system may determine the location of the patient ID tag in the healthcare facility within one foot or less of the patient ID tag's actual location. The computer of the high-accuracy location system may be configured to determine whether a patient has entered a bathroom of the healthcare facility. If the patient has entered the bathroom, the computer of the high-accuracy locating system may determine whether the patient has fallen based on at least one of the following: an elevation of the patient ID tag relative to a reference plane violating a height threshold or an elevation drop of the patient ID tag over a time period exceeding a drop threshold.

In some embodiments, the height threshold may be defined by a height of a seat of a toilet in the bathroom. The reference plane may be defined as a substantially horizontal plane that passes through at least two transceivers mounted at a substantially equivalent distance above a floor of the bathroom. Alternatively or additionally, the reference plane may be defined as a substantially horizontal plane that passes through at least two transceivers mounted at a substantially equivalent distance below a floor of the bathroom. Optionally, if the computer determines that the patient has fallen, the computer may initiate an alert to a nurse's station or to a wireless communication device of a caregiver.

If desired, the computer of the high-accuracy locating system also may monitor an amount of time that the patient has been in the bathroom. The computer of the high-accuracy locating system may initiate an alert to a nurse's station or to a wireless communication device of a caregiver if the amount of time that the patient has been in the bathroom exceeds a time threshold even if the height threshold is not violated and even if the drop threshold is not exceeded.

In some embodiments, the computer may track a number of times that the patient uses the bathroom or enters the bathroom. The computer may initiate an alert to a nurse's station or to a wireless communication device of a caregiver if the number of times that the patient uses or enters the bathroom exceeds a predetermined threshold within a predetermined period of time. Alternatively or additionally, the computer may initiate an alert to housekeeping if the number of times that the patient uses or enters the bathroom exceeds a predetermined threshold. The predetermined threshold may be at least three times, for example.

It is contemplated by this disclosure that the computer of the high-accuracy location system may not determine whether the elevation of the patient ID tag relative to the reference plane violates the height threshold and may not determine if the elevation drop of the patient ID tag over the time period exceeds the drop threshold if the patient is outside of the bathroom. Thus, the computer of the high-accuracy location system may determine the elevation of the patient ID tag relative to the reference plane only after the patient is determined to be in the bathroom. If desired, the computer may initiate an alert to a nurse's station or to a wireless communication device of a caregiver after the computer determines that the patient ID tag has violated the height threshold for a predetermined period of time.

In some embodiments, the plurality of transceivers and the tag transceiver may communicate via ultra-wideband (UWB) signals. Alternatively or additionally, location of the patient ID tag may be determined by the computer using two way ranging and time difference of arrival (TDOA) techniques. Further alternatively or additionally, the computer may use signals from only a subset of the plurality of transceivers to determine the location of the patient ID tag. The subset may be determined based on signal strength of signals from the tag transceiver to the plurality of transceivers. For example, the subset may include at least three transceivers from the plurality of transceivers having highest signal strength values as compared to others of the plurality of transceivers.

According to another aspect of the present disclosure, a bathroom monitoring system may include a computer, a plurality of transceivers that may be mounted at fixed locations throughout the healthcare facility and that may be communicatively coupled to the computer. The system further may include a patient identification (ID) tag that may be worn by a patient. The patient ID tag may have a first tag transceiver that may be configured to communicate with the plurality of transceivers. The system also may have a housekeeper identification (ID) tag that may be worn by a housekeeper. The housekeeper ID tag may have a second tag transceiver that may be configured to communicate with the plurality of transceivers. The plurality of transceivers and the computer may cooperate to form a high-accuracy locating system that may be operable to determine a location of the patient ID tag and the housekeeper ID tag within one foot or less of the patient ID tag's and housekeeper ID tag's actual location, respectively. The high-accuracy locating system may monitor a location of the patient via signals from the first tag transceiver to determine whether a patient has entered a bathroom. The computer may increment a counter to count a number of times that the patient enters the bathroom and may initiate an alert to the housekeeper if the number of times that the patient enters the bathroom exceeds a predetermined threshold. The high-accuracy location system may monitor a location of the housekeeper via signals from the second tag transceiver. The computer may reset the counter to zero in response to the housekeeper entering the bathroom.

In some embodiments, the predetermined threshold may be three times. Optionally, the computer may track an amount of time that the patient has been in the bathroom, may compare the amount of time to a predetermined time, and may initiates an alert to a caregiver if the amount of time exceeds the predetermined time. Further optionally, the computer of the high-accuracy locating system may determine that the patient has fallen based on an elevation of the patient ID tag relative to a reference plane violating a height threshold. The height threshold may be defined by a height of a seat of a toilet in the bathroom, for example.

It is contemplated by this disclosure that the reference plane may be defined as a substantially horizontal plane that passes through at least two transceivers mounted at a substantially equivalent distance above a floor of the bathroom. Alternatively or additionally, the reference plane may be defined as a substantially horizontal plane that passes through at least two transceivers mounted at a substantially equivalent distance below a floor of the bathroom. If the computer determines that the patient has fallen, the computer may initiate an alert to a nurse's station or to a wireless communication device of a caregiver.

In some embodiments, the computer of the high-accuracy locating system may determine that the patient has fallen based on an elevation of the patient ID tag relative to a reference plane violating a height threshold for a predetermined amount of time. Alternatively or additionally, the computer may track a rate of change in an elevation of the patient ID tag to determine whether the patient has fallen. The computer may initiate an alert to a nurse's station or to a wireless communication device of a caregiver if the computer determines that the patient has fallen. If desired, the computer may initiate an alert to a nurse's station or to a wireless communication device of a caregiver if the number of times that the patient uses or enters the bathroom exceeds a predetermined threshold within a predetermined period of time.

It is within the scope of this disclosure that the bathroom monitoring system may further include a caregiver identification tag that may include a caregiver transceiver to communicate with the high-accuracy locating system. The computer may also increment the counter in response to the caregiver entering the bathroom.

In some embodiments, the first and second tag transceivers may communicate with the plurality of transceivers via ultra-wideband (UWB) signals. Alternatively or additionally, the locations of the patient ID tag and the housekeeper ID tag may be determined by the computer using two way ranging and time difference of arrival (TDOA) techniques. Further alternatively or additionally, the computer may use signals from only a subset of the plurality of transceivers to determine the locations of the patient ID tag and the housekeeper ID tag. The subset may be determined based on signal strength of signals from the first tag transceiver and the second tag transceiver to the plurality of transceivers. For example, the subset may include at least three transceivers from the plurality of transceivers having highest signal strength values as compared to others of the plurality of transceivers.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
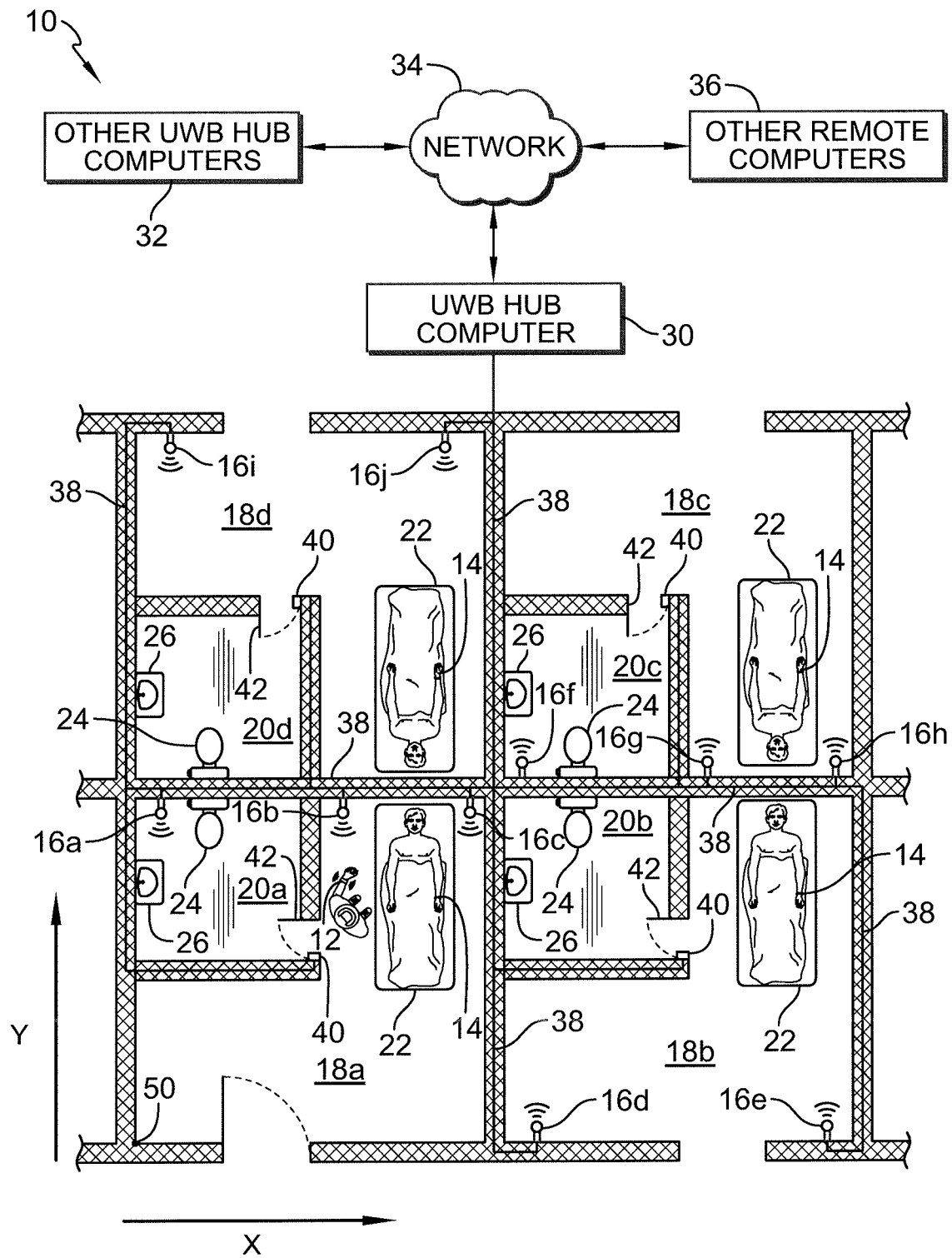
FIG. 1 is a diagrammatic top plan view of patient rooms of a healthcare facility showing a high-accuracy locating system operating to track the locations of patients having patient identification (ID) tags and caregivers having caregiver ID tags in the patient rooms and bathrooms of the patient rooms.
Figure 2:
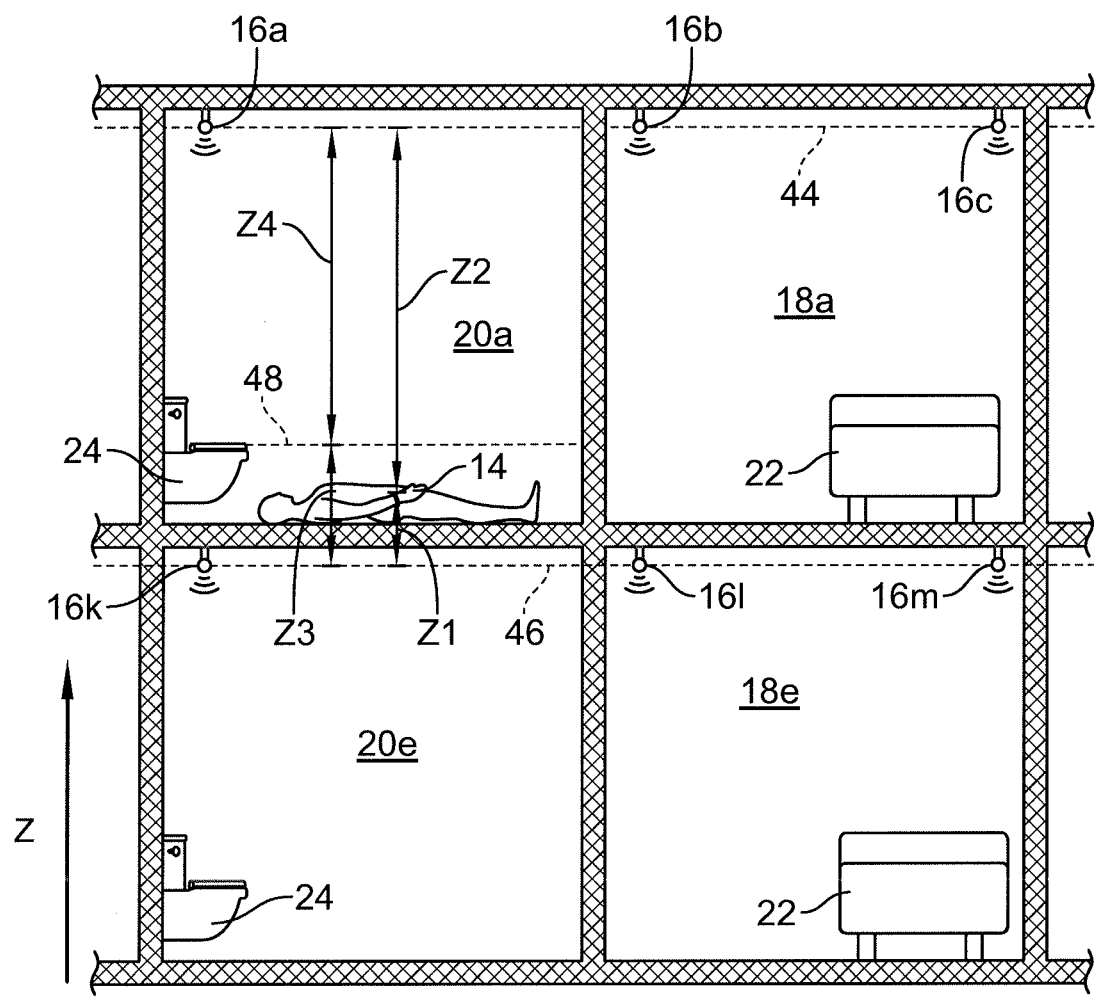
FIG. 2 is a diagrammatic elevation view of two patient rooms and bathrooms on two different floors showing a patient that has fallen to the floor in one of the bathrooms and showing reference planes (in phantom) extending through transceivers of the high-accuracy locating system on each of the two floors and showing a height threshold (in phantom) extending through a toilet in the bathroom in which the patient has fallen.

A system 10 to track the whereabouts of caregivers and patients in a health care facility such as a hospital or nursing home includes mobile staff tags 12 worn by staff members such as caregivers and housekeepers, and mobile patient tags 14 worn by patients as shown in FIG. 1. System 10 also has a multitude of transceivers, illustratively indicated as transceivers 16a-16j in FIG. 1. Transceivers 16a-16j are shown dispersed throughout four patient rooms 18a-18d located on the same floor of the healthcare facility. Each patient room 18a-18d has its own bathroom 20a-20d in the illustrative example. In FIG. 2, a patient room 18e with its respective bathroom 20e is located on the floor of healthcare facility below the floor of FIG. 1. In FIG. 2, bathroom 20e is located directly beneath bathroom 20a. Additional transceivers 16k-16m are also shown in FIG. 2. It should be understood that FIGS. 1 and 2 are generic representations of a floor plan of a healthcare facility and so other floor plan configurations of patient rooms and bathrooms are, of course, within the scope of the present disclosure.

Tags 12, 14 and transceivers 16a-16m each include a housing that contains associated circuitry. The circuitry of tags 12, 14 and transceivers 16a-16m includes for example a processor such as a microprocessor or microcontroller or the like, memory for storing software, and communications circuitry including a transmitter, a receiver and at least one antenna, for example. Tags 12, 14 also include structure to enable attachment to caregivers, patients, and other hospital personnel such as housekeepers. For example, tags 12 may include a necklace so that a caregiver can wear the tag 12 around their neck or may include a clip so that the caregiver can attach the tag 12 to their clothing. Each of tags 14 may include a wristband so that the tags 14 can be worn on the wrists of the associated patients. Transceivers 16a-16m each include mounting hardware, such as brackets or plates or the like, in some embodiments, to permit the transceivers 16a-16m to be mounted at fixed locations in the rooms 18a-18e, 20a-20e of the healthcare facility with fasteners such as screws or the like.

Each of rooms 18a-18e has a patient bed 22 located therein to support a respective patient during their stay in the healthcare facility as shown in FIGS. 1 and 2. In the illustrative example, each bathroom 20a-20e has a toilet 24 and a sink 26. In other embodiments, one or more of bathrooms 20a-20e includes a shower. System 10 further includes a hub computer 30 which is communicatively coupled to other hub computers 32 of system 10 via a network 34 of the healthcare facility. In the illustrative example, system 10 is also communicatively coupled to other remote computers 36 of the healthcare facility. Such other remote computers 36 include, for example, nurse call computers, electronic medical records (EMR) computers, admission/discharge/transfer (ADT) computers, a locating server for handling data from hubs 30, 32, and the like.

As shown in FIG. 1, system 10 further includes electrical lines 38 that electrically couple each of transceivers 16a-16j to hub computer 30. For ease of illustration, the electrical lines 38 are depicted as being routed through the walls of the various rooms 18a-18d. However, it should be understood that such lines 38 may be routed over a ceiling and/or under a floor of the respective room 18a-18d at the discretion of the system designer for any given healthcare facility. Transceivers 16a-16m communicate wirelessly with tags 12, 14 using radio frequency (RF). It is known that RF signals are able to pass through walls, ceilings, floors, and other objects. Thus, according to this disclosure, it is not required that each room 18a-18e and/or bathroom 20a-20e has a transceiver located therein. In fact, each of bathrooms 20b, 20d do not have any transceiver located therein in the illustrative example.

According to this disclosure, system 10 operates as a high-accuracy locating system which is able to determine the location of each tag 12, 14 that is in communication with at least three of transceivers 16a-16m within one foot (30.48 cm) or less of the tag's actual location. System 10 is operable to determine the location of tags 12, 14 in 3-dimensional space. Accordingly, FIG. 1 shows X and Y directions and FIG. 2 shows a Z direction which corresponds to the height direction in the healthcare facility. One example of a high-accuracy locating system contemplated by this disclosure is an ultra-wideband (UWB) locating system. UWB locating systems operate within the 3.1 gigahertz (GHz) to 10.6 GHz frequency range. Suitable transceivers 16a-16m in this regard include WISER Mesh Antenna Nodes and suitable tags 12, 14 in this regard include Mini tracker tags, all of which are available from Wiser Systems, Inc. of Raleigh, N.C. and marketed as the WISER LOCATOR™ system.

In some embodiments, system 10 uses 2-way ranging, clock synchronization, and time difference of arrival (TDoA) techniques to determine the locations of tags 12, 14 in the X, Y, and Z dimensions. See, for example, International Publication No. WO 2017/083353 A1, which is hereby incorporated by reference herein in its entirety for all that it teaches to the extent not inconsistent with the present disclosure which shall control as to any inconsistencies, for a detailed discussion of the use of these techniques in a UWB locating system. Using these techniques, distances between the stationary transceivers 16a-16m and the various mobile tags 12, 14 are determined based on bidirectional wireless signals communicated between tags 12, 14 and transceivers 16a-16m. For example, the distance from each transceiver 16a-16m to any particular tag can be resolved onto the X-Y plane as a circle having a radius equal to the distance and having its center at the particular transceiver 16a-16m. The actual location of the mobile tag 12, 14 is determined based on the point of intersection of three or more of the circles defined by radii from three or more corresponding transceivers 16a-16m.

It should be appreciated that, unless a tag 12, 14 is midway between two transceivers 16a-16m on a straight line connecting the two transceivers 16a-16m (in which case the two circles generated will be tangent to each other at a single point), then two circles that are generated from the two transceivers 16a-16m will intersect at two points such that a circle generated from a third transceiver is needed to determine which of the two points is the one corresponding to the location of the tag 12, 14. Generating fourth, fifth, sixth, etc. circles having other transceivers 16a-16m as their respective centers will further increase the accuracy of determining the actual location of the particular tag 12, 14. Due to small errors introduced by refraction of the RF signal through solid objects, including walls, people, equipment, etc., the three or more circles in many instances will not intersect at exactly the same point and so interpolation between clusters of circle intersections is performed to arrive at the calculated location of the particular mobile tag 12, 14 of interest on the X-Y plane. These considerations are discussed in International Publication No. WO 2017/083353 A1 which is already incorporated by reference herein.

Tracking the locations of multiple mobile tags 12, 14 in substantially real time using 2-way ranging, clock synchronization, TDoA, resolution of circles onto the X-Y plane, and interpolating intersection point clusters of the circles requires a large amount of computational power by hub computers 30, 32 and/or the associated locating server 36. Thus, each hub computer 30, 32 receives incoming data from a predetermined number of transceivers 16a-16m. In the illustrative example of FIG. 1, hub computer 30 receives data from ten transceivers 16a-16j. TDC Acquisition Holdings, Inc. of Huntsville, Ala. which does business as Time Domain, makes a hub computer (referred to as the PLUS Synchronization Distribution Panel) that is capable of receiving incoming data from up to 144 transceivers. The locating server or computer 36, in turn, receives data from the various hubs 30, 32 and tracks or monitors the locations of tags 12, 14 in the healthcare facility.

According to this disclosure, when patients wearing tags 14 enter into respective bathrooms 20a-20e while unattended, system 10, or more particularly the respective hub computer 30, 32 and/or the associated locating server 36 of system 10, enters into a falls monitoring mode of operation to monitor the height of tag 14 in the Z-dimension. That is, when a patient uses one of bathrooms 20a-20e without any caregiver tag 12 also being detected in the same bathroom 20a-20e with the patient, system 10 enters into the falls monitoring mode. In some embodiments, system 10 includes a door monitor or sensor 40 for each bathroom 20a-20e. Sensors 40 each provide a signal indicative or whether the associated door 42 is closed. In such embodiments, system 10 enters the falls monitoring mode if any patient is in the respective bathroom 20a-20e without a caregiver and with the corresponding door 42 being closed as sensed by the associated sensor 40. If the bathroom door is open, caregivers are able to see whether the patient has fallen if a caregiver is present in the adjacent room 18a-18e, for example.

To determine that the patient is in one of bathrooms 20a-20e based on signals from the respective tag 14 of the patient, one or more of computers 30, 32, 36 compares the X and Y coordinates of the respective patient tag 14 with X and Y coordinate ranges that correspond to the various bathrooms 20a-20e. Thus, an arbitrary origin of the X-Y coordinate system is established on the floor plan of the healthcare facility for each floor. Using bathroom 20a as an example, an origin 50 is established at the lower left corner of room 18a as shown in FIG. 1. Assuming that room 18a is a 20 foot by 20 foot room with bathroom 20a occupying a 10 foot by 10 foot space of the room 18a, then tag 14 and the associated patient is considered to be in the bathroom if the X coordinate is between 0 feet and 10 feet and the Y coordinate is between 10 feet and 20 feet, or more precisely, if the X coordinate is between 0 inches and 120 inches and the Y coordinate is between 120 inches and 240 inches. These X, Y coordinates for bathroom 20a correspond to the upper left quadrant of room 18a in the illustrative example. In a similar manner, the X, Y coordinates corresponding to bathrooms 20b-20d are also established relative to origin 50.

It should be appreciated that the room geometry and floor plan shown in FIG. 1 is a simplified example for purposes of illustrating the general concept of how one or more of computers 30, 32, 36 are programmed to determine whether a tag 14 is in a bathroom 20a-20e. The placement of origin 50 in any given floor plan of any given health care facility is at the discretion of the system programmer and the X, Y coordinate ranges corresponding to bathrooms of any given healthcare facility will vary from facility to facility based on room geometry. In some embodiments, one of transceivers 16a-16m may be chosen as the origin for the X, Y coordinate system if desired.

After system 10 enters into the falls monitoring mode, one or more of computers 30, 32, 36 of system 10 determines whether a patient has fallen in the particular bathroom 20a-20e based on the position of the respect tag 14 in the Z-dimension as compared to a height threshold measured from a substantially horizontal reference plane. Referring to FIG. 2, a substantially horizontal first reference plane 44 is defined through the transceivers 16a-16j mounted in the rooms of the illustrative upper floor of the healthcare facility and a substantially horizontal second reference plane 46 is defined through transceivers 16k-16m mounted in the rooms of the lower floor of the healthcare facility. In FIG. 2, only transceivers 16a, 16b, 16c are shown in connection with the upper floor and only transceivers 16k, 16l, 16m are shown in the connection with the lower floor. However, it should be understood that planes 44, 46 pass through other transceivers mounted in the rooms of the respective upper and lower floors. To establish substantially horizontal planes 44, 46, the associated transceivers should be mounted at substantially the same elevations, such as may be measured downwardly from a ceiling of the upper or lower floor or upwardly from the floor of the upper or lower floor.

In the illustrative example of FIG. 2, a threshold plane 48 is also established and is shown to be about the height of a seat of toilet 24. Plane 48 may be established at other heights in other embodiments at the discretion of the system designer. Thus, plane 48 may be at some arbitrary height so as to be above the toilet seat or below the toilet seat. As a general proposition, when tag 14 of the patient is below plane 48 it is an indication that the patient has likely fallen and when the tag 14 of the patient is above plane 48 it is an indication that the patient likely has not fallen. To determine whether tag 14 is above or below plane 48 in the Z-dimension, calculations can be made from either of the reference planes 44, 46.

The reference plane 44, 46 on which to base the calculations can be selected based on signal strength between tag 14 and receivers 16a-16m, for example. That is, the transceivers on the upper floor are used if the signal strengths between some or all of the upper floor transceivers and tag 14 are larger than those between some or all of the lower floor transceivers and tag 14, and vice versa. In some embodiments, the three transceivers 16a-16m having the highest signal strength may be used regardless of whether they are located on the upper or lower floor. Referring to FIG. 2, a likely scenario is that transceivers 16a, 16k and 16l are the three transceivers having the highest signal strength with tag 14 in bathroom 20a. In that instance, the Z coordinate of tag 14 in FIG. 2 is determined using transceivers 16a, 16k and 16l. In some embodiments, more than three of transceivers 16a-16m are used to determine the Z coordinate of tag 14.

In some embodiments, to determine whether or not tag 14 is below the threshold plane 48 using reference plane 46, the hub computer 32 associated with bathroom 20e and/or the server 36 compares distance Z1, which is defined as the substantially vertical distance between reference plane 46 and tag 14, with distance Z3 which is a threshold distance defined substantially vertically between plane 46 and plane 48. If Z1 is less than Z3, then tag 14 is below plane 48 and if Z1 is greater than Z3, then tag 14 is above plane 48. If Z1 equals Z3, then the system designer can decide whether or not that particular condition, as rare as it would likely occur, is considered to be indicative of the patient having fallen.

In some embodiments, to determine whether or not tag 14 is below the threshold plane 48 using reference plane 44, the hub computer 30 associated with bathroom 20a and/or the server 36 compares distance Z2, which is defined as the substantially vertical distance between reference plane 44 and tag 14, with distance Z4 which is a threshold distance defined substantially vertically between plane 44 and plane 48. If Z2 is greater than Z4, then tag 14 is below plane 48 and if Z2 is less than Z4, then tag 14 is above plane 48. If Z2 equals Z4, then the system designer can decide whether or not that particular condition, as rare as it would likely occur, is considered to be indicative of the patient having fallen.

In some embodiments, the Z coordinate of tag 14 is determined relative to the established origin 50 in the Z dimension and then compared to Z coordinate ranges corresponding to tag 14 being below reference plane 48 and above the corresponding floor surface. Thus, in each of the above described examples, the basic idea is that an elevation of tag 14 is compared to a threshold in the Z-dimension to determine if the Z dimension threshold is violated in which case it can be concluded that the patient wearing tag 14 has likely fallen in the bathroom.

In the illustrative example, tag 14 is included as part of a wrist band worn by the patient. It is possible that, while the patient is in the bathroom, including while sitting on the toilet, the patient may temporarily reach down below plane 48 with their hand to pick up an item from the floor or scratch their ankle or for some other reason. Thus, it is contemplated by this disclosure that, in some embodiments, before a falls determination is made with regard to the patient, tag 14 must be determined to be below plane 48 for a threshold period of time, such as about 10 seconds to just to pick an arbitrary number. Time thresholds above and below about 10 seconds, such as between about 5 seconds and about 30 seconds just to give another set of arbitrary examples, are within the scope of this disclosure.

Figure 3:
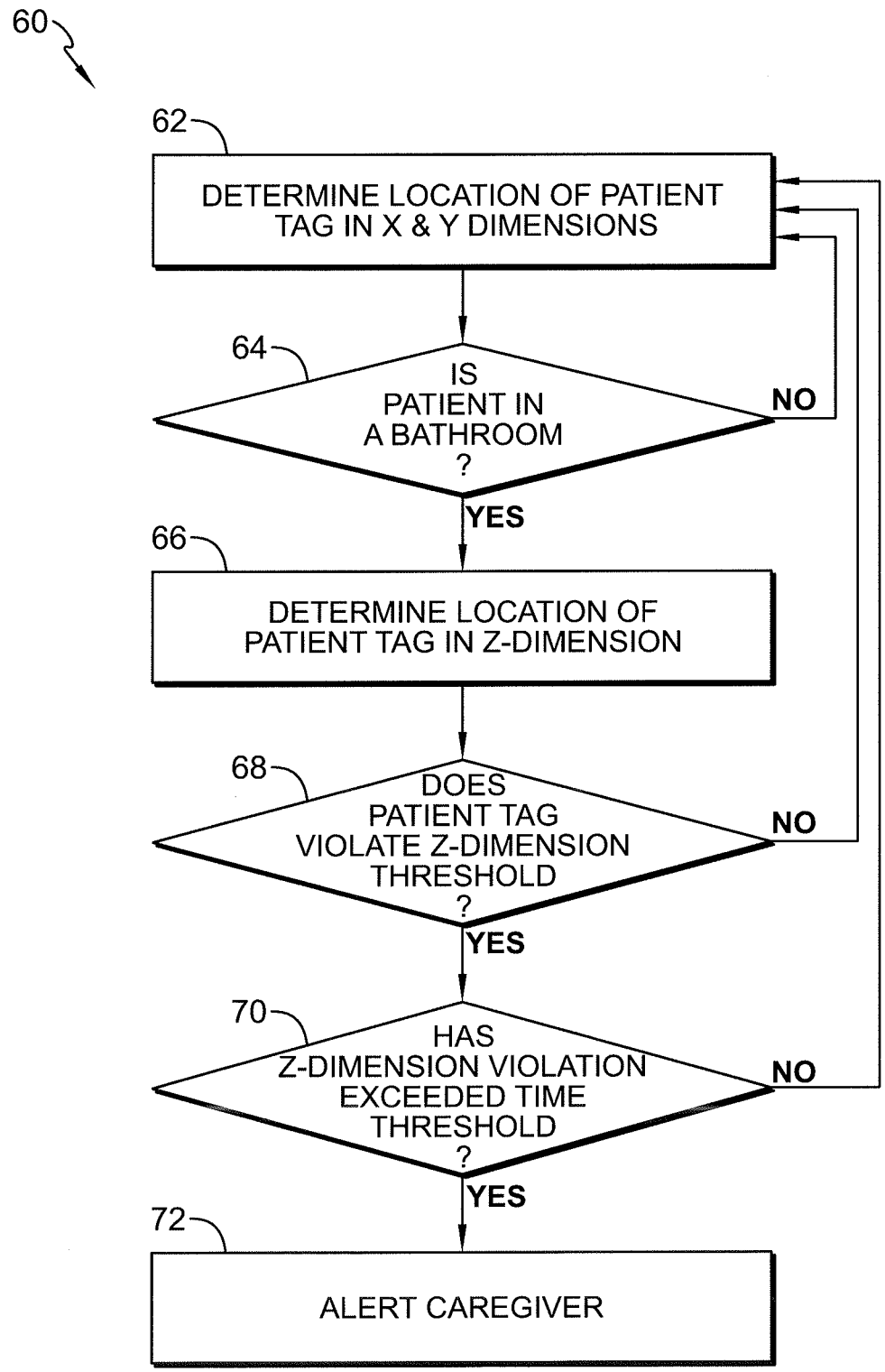
FIG. 3 is a block diagram showing a first flow chart that is representative of an algorithm to determine if a patient ID tag violates an elevation criteria which is indicative that a corresponding patient has fallen in one of the bathrooms.

Referring now to FIG. 3, a flow chart of an algorithm 60 that is illustrative of the above described steps for monitoring patient falls in bathrooms 20a-20e is provided. Algorithm 60 is embodied as software on one or more of computers 30, 32, 36. In one embodiment, for example, all steps of algorithm 60 are performed on a locating server 36 that receives location data from each of hubs 30, 32. In other embodiments, some steps of algorithm 60 are performed on hubs 30, 32, some are performed on the locating server 36, and optionally, some steps are performed on some other server or computer 36 such as a server 36 of a nurse call system or electronic medical records (EMR) server. Algorithm 60 is executed in connection with each tag 14 being monitored. Thus, the discussion below relates to a single tag 14, but is applicable to all tags 14 being monitored in system 10.

Step 62 begins the algorithm 60 by determining the location of a patient tag 14 in the X and Y dimensions. After the X, Y dimension location (e.g., the X and Y coordinates) of the tag 14 is determined at step 62, algorithm 60 proceeds to step 64 to determine whether the tag 14, and therefore the associated patient, is in one of bathrooms 20a-20e. If not, algorithm 60 loops back to step 62 and proceeds from there. If the patient is determined to be in one of the bathrooms 20a-20e, algorithm 60 proceeds to step 66 to determine a location of the tag 14 in the Z dimension. This Z dimension determination can be in accordance with any of the examples given above with regard to reference planes 46, 48 or with regard to a substantially horizontal plane passing through the origin 50 or with regard to any other substantially horizontal reference plane chosen by the system designer (e.g. sea level or a floor of the healthcare facility).

After the Z dimension of the tag 14 is determined, the algorithm 60 proceeds to step 68 and determines whether the tag 14 violates the Z-dimension threshold such as being below plane 48 in the above described example. If the location of tag 14 in the Z dimension does not violate the Z-dimension threshold, then algorithm 60 loops back to step 62 and proceeds from there. If the location of tag 14 violates the Z-dimension threshold, the algorithm 60 proceeds to step 70 to determine whether the Z-dimension threshold violation has exceeded a time threshold. If not, the algorithm 60 loops back to step 62 and proceeds from there. If the time threshold at step 70 has been exceeded, then algorithm 70 proceeds to step 72 to alert a caregiver that the patient associated with the violating tag 14 has likely fallen in the bathroom 20a-20e in which that particular patient is located. In a variant of algorithm 60, step 70 is omitted and the alert to a caregiver at step 72 is performed immediately after step 68 in response to the tag 14 position in the Z dimension being violated. Such a variant algorithm may be desirable, for example, if tag 14 is worn on a necklace around the patient's neck or is attached to an upper torso covering portion of a gown of the patient.

The present disclosure contemplates several ways in which to alert a caregiver of a patient bathroom fall in accordance with step 72. For example, the locating server 36 sends a message to a nurse call server 36 in some embodiments and the nurse call server 36 initiates an alert message to a mobile device carried by one or more caregivers assigned to the particular patient. See U.S. Pat. No. 7,319,386, which is hereby incorporated by reference herein in its entirety for all that it teaches to the extent not inconsistent with the present disclosure which shall control as to any inconsistencies, for a discussion of the use of a nurse call system to send alert messages to pagers, telephone handsets, communication badges, mobile phones, and the like. Alternatively or additionally, the locating server 36 initiates an alert message to a caregiver's mobile device without involving any nurse call system server 36. Reference number 36 is used in FIG. 1 to represent a multitude of computer devices including computer devices of nurse call systems, EMR systems, and other types of healthcare information systems such as pharmacy systems, laboratory systems, and the like. In addition to, or in lieu of, displaying visual alerts (e.g., illuminating a light or displaying a message) on various devices just described, an audible alert such as an alert tone or verbal message may be emitted from one or more of the various devices that alert caregivers in connection with step 72 of algorithm 60.

In some embodiments, an indicator light, which is sometimes referred to as a dome light, of a nurse call system is illuminated outside the patient room 18a-18e to alert caregivers in the vicinity of the light of the bathroom fall alert in connection with step 72 of algorithm 60. See U.S. Pat. No. 8,384,526, which is hereby incorporated by reference herein in its entirety for all that it teaches to the extent not inconsistent with the present disclosure which shall control as to any inconsistencies, for a discussion of a suitable indicator light of a nurse call system. Messages regarding a bathroom falls alert appear on other displays, such as a master nurse station computer 36, a status board display 36, one or more graphical room stations 36 of a nurse call system, and one or more staff stations 36 of a nurse call system are also examples of caregiver alerts of step 72 of algorithm 60 in some embodiments. Further details of these devices used in nurse call systems as well as other types of related equipment included in various embodiments of nurse call systems (as well as network 34, in general) can be found in U.S. Pat. Nos. 7,538,659; and 5,838,223 and in U.S. Patent Application Publication Nos. 2009/0217080; 2009/0212956; and 2009/0212925, each of which is hereby incorporated by reference herein in its entirety for all that it teaches to the extent not inconsistent with the present disclosure which shall control as to any inconsistencies, as well as in U.S. Pat. Nos. 8,384,526 and 7,319,386 which are already incorporated herein by reference.

Figure 4:
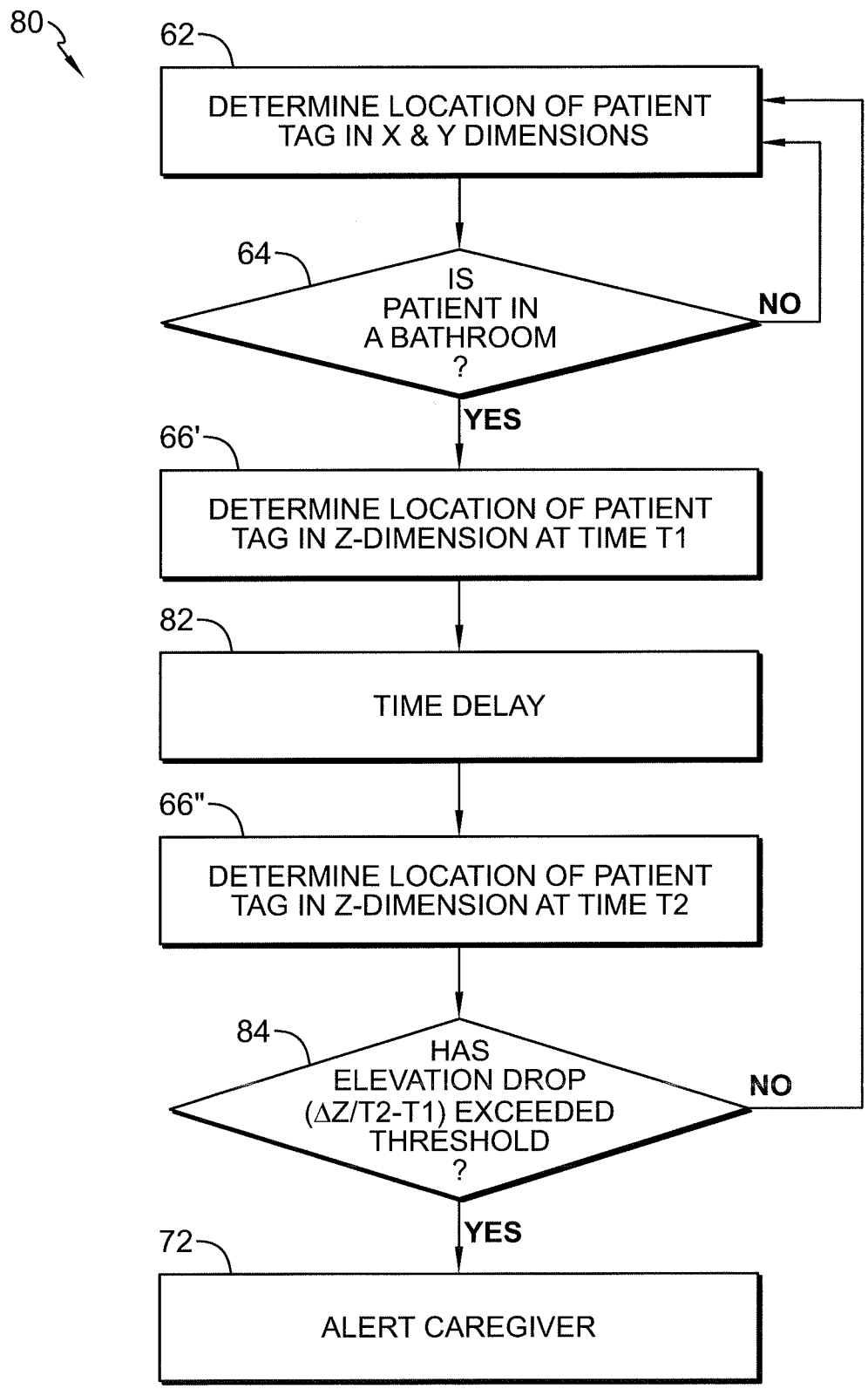
FIG. 4 is a block diagram showing a second flow chart that is representative of an algorithm to determine if a patient ID tag violates an elevation drop criteria which is indicative that a corresponding patient has fallen in one of the bathrooms.

The present disclosure further contemplates an algorithm 80, shown in FIG. 4, in which a rapid drop of tags 14 while in bathrooms 20a-20e and while the respective patient is unattended by a caregiver and, in some embodiments, while the corresponding bathroom door 42 is closed as sensed by the associated sensor 40. Algorithm 80 is discussed below in connection with a single tag 14, but is applicable to all tags 14 being monitored in system 10 in those embodiments including algorithm 80. As was the case with algorithm 60, algorithm 80 is embodied as software on one or more of computers 30, 32, 36.

The first two steps 62, 64 of algorithm 80 are the same as the first two steps 62, 64 of algorithm 60 described above. Thus, the description of these two steps 62, 64 does not need to be repeated. If the patient is determined to be in the bathroom at step 64, then algorithm 80 proceeds to step 66' in with the location of tag 14 in the Z dimension is determined at time T1. This Z-dimension determination can be in accordance with any of the examples given above with regard to reference planes 46, 48 or with regard to a substantially horizontal plane passing through the origin 50 or with regard to any other substantially horizontal reference plane chosen by the system designer. However, according to step 66', a time T1 is associated with the particular Z-dimension determination.

After the Z-dimension determination is made at block 66', algorithm 80 proceeds to block 82 and implements a time delay. The time delay is relatively short, such as on the order of about an ⅛ second to about 1 second, in some embodiments. However, other time delays that are less than about ⅛ second or more than about 1 second are within the scope of the present disclosure at the option of the system designer. After the time delay of block 82, algorithm proceeds to block 66" and determines the location of tag 14 in the Z-dimension at time T2. Time T2 occurs the time delay after time T1. After the Z-dimension at time T2 is determined, the algorithm 80 proceeds to step 84 and a determination is made as to whether the elevation drop (e.g., change in Z-dimension/(T2−T1) or dZ/dt) has exceeded a threshold.

If the reference plane being used is below the tag 14, then assuming tag 14 has moved downwardly in elevation such that the elevation at time T2 is less than the elevation at T1, then dZ/dt should be a negative number. However, if the reference plane being used is above the tag, then assuming tag 14 has moved downwardly in elevation such that the Z-dimension measured downwardly from the overlying reference plane at time T2 is more than the Z-dimension measured downwardly from the overlying reference plane at time T1, then dZ/dt should be a positive number. In either case, dZ/dt can be ignored in the event that it indicates upward movement of tag 14 rather than downward movement. That is, in the case of a reference plane below tag 14, then a positive dZ/dt indicates upward movement of tag 14 and, in the case of a reference plane above tag 14, then a negative dZ/dt indicates upward movement of tag 14.

From the foregoing discussion, the statement at step 84 that the elevation drop dZ/dt is being checked to see if it has "exceeded" a threshold means that, if the reference plane is below the tag 14, then the elevation drop dZ/dt is considered to have exceeded the threshold if it is more negative than the threshold which is a negative number and, if the reference plane is below the tag 14, then the elevation drop dZ/dt is considered to have exceeded the threshold if it is more positive than the threshold which is a positive number. In either case, the system designer needs to be cognizant of the reference plane location relative to the tag 14 in connection with programming the mathematical rules associated with step 84 of algorithm 80.

If at step 84 the elevation drop, dZ/dt, has not exceeded the threshold, then algorithm loops back to step 62 and proceeds from there. If at step 84 the elevation drop, dZ/dt, has exceeded the threshold, then algorithm 80 proceeds to step 72 to alert a caregiver that the patient in the bathroom has likely fallen. The various types of caregiver alerts discussed above in connection with step 72 of algorithm 60 are equally applicable to step 72 of algorithm 80. Algorithm 80 permits the elevation drop, dZ/dt, of each tag 14 to be determined without the use of an accelerometer in the tags 14. By avoiding the use of an accelerometer in tags 14, the circuitry of tags 14 does not need to be as complex and expensive as the prior art tags 14 that include an accelerometer.

Figure 5:
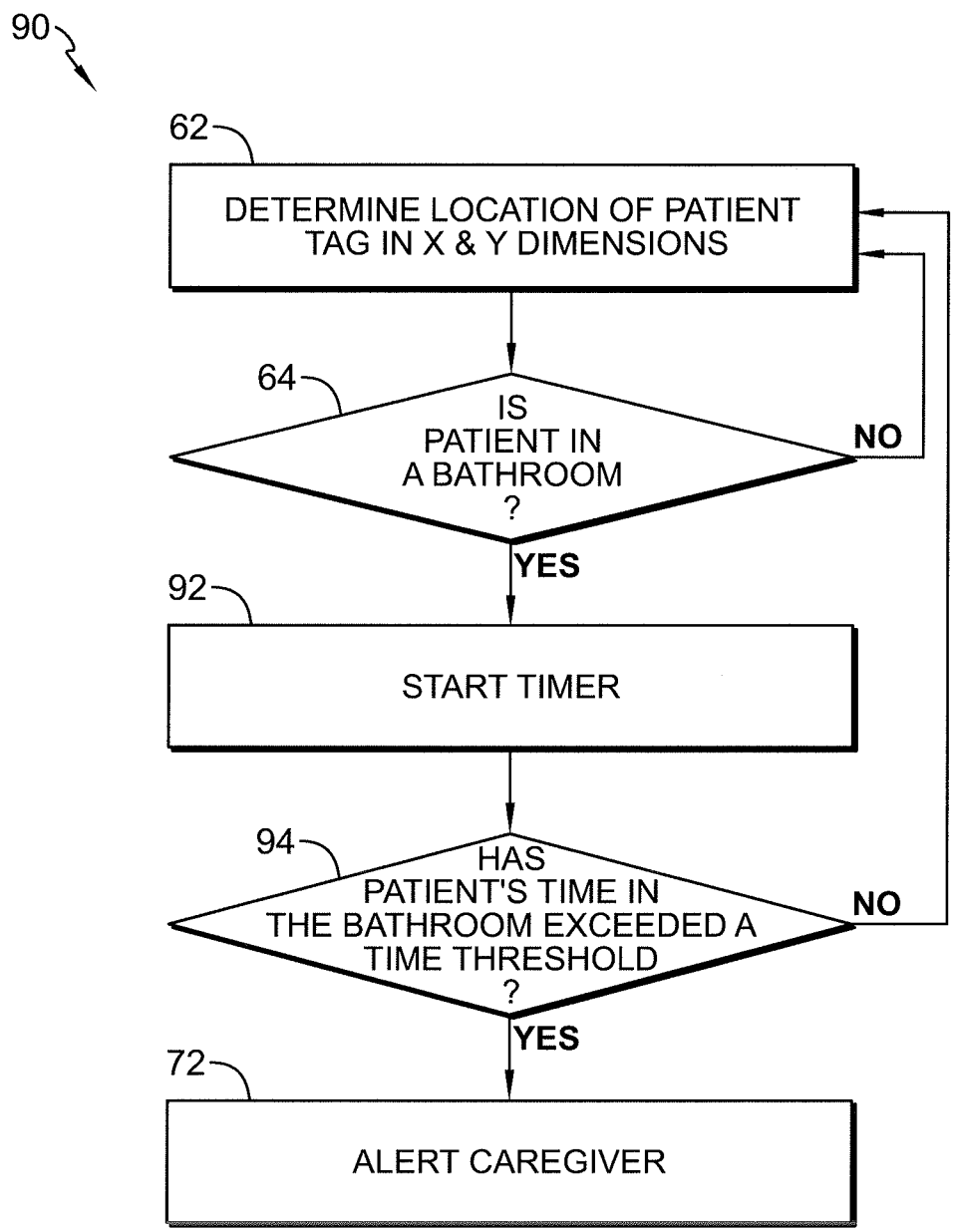
FIG. 5 is a block diagram showing a third flow chart that is representative of an algorithm to determine if a patient ID tag violates a time threshold which is indicative that a patient in one of the bathrooms may need assistance.

The present disclosure further contemplates an algorithm 90, shown in FIG. 5, in which a total time of tags 14 being in respective bathrooms 20a-20e is monitored and, in some embodiments, while the respective patient is unattended by a caregiver and/or while the corresponding bathroom door 42 is closed as sensed by the associated sensor 40. Algorithm 90 is discussed below in connection with a single tag 14, but is applicable to all tags 14 being monitored in system 10 in those embodiments including algorithm 90. As was the case with algorithm 60, algorithm 90 is embodied as software on one or more of computers 30, 32, 36.

The first two steps 62, 64 of algorithm 90 are the same as the first two steps 62, 64 of algorithm 60 described above. Thus, the description of these two steps 62, 64 does not need to be repeated. If the patient is determined to be in the bathroom at step 64, then algorithm 90 proceeds to step 92 to start a timer which keeps track of the total or overall amount of time that tag 14, and therefore, the patient wearing tag 14, has been in the bathroom 20a-20e since first entering it. At step 94, the timer is monitored and a determination is made as to whether the patient's time in the bathroom has exceeded a time threshold. The time threshold may be on the order of about 20 minutes to about 30 minutes just to give a couple of arbitrary examples. A time threshold lower than 20 minutes or greater than 30 minutes is within the scope of this disclosure.

If the patient's time in the bathroom has not exceeded the time threshold, then algorithm 90 loops back to step 62 and proceeds from there. If the patient's time in the bathroom has exceeded the time threshold at step 94, then algorithm proceeds to step 72 to alert a caregiver that the patient has been in the bathroom for an amount of time that exceeds the time threshold. The various types of caregiver alerts discussed above in connection with step 72 of algorithm 60 are equally applicable to step 72 of algorithm 90. Algorithm 90, therefore, results in an alert to one or more caregivers if a patient has been in one of bathrooms 20a-20e for an extended period of time and may need assistance even though there is no indication that the patient may have fallen in the bathroom.

Figure 6:
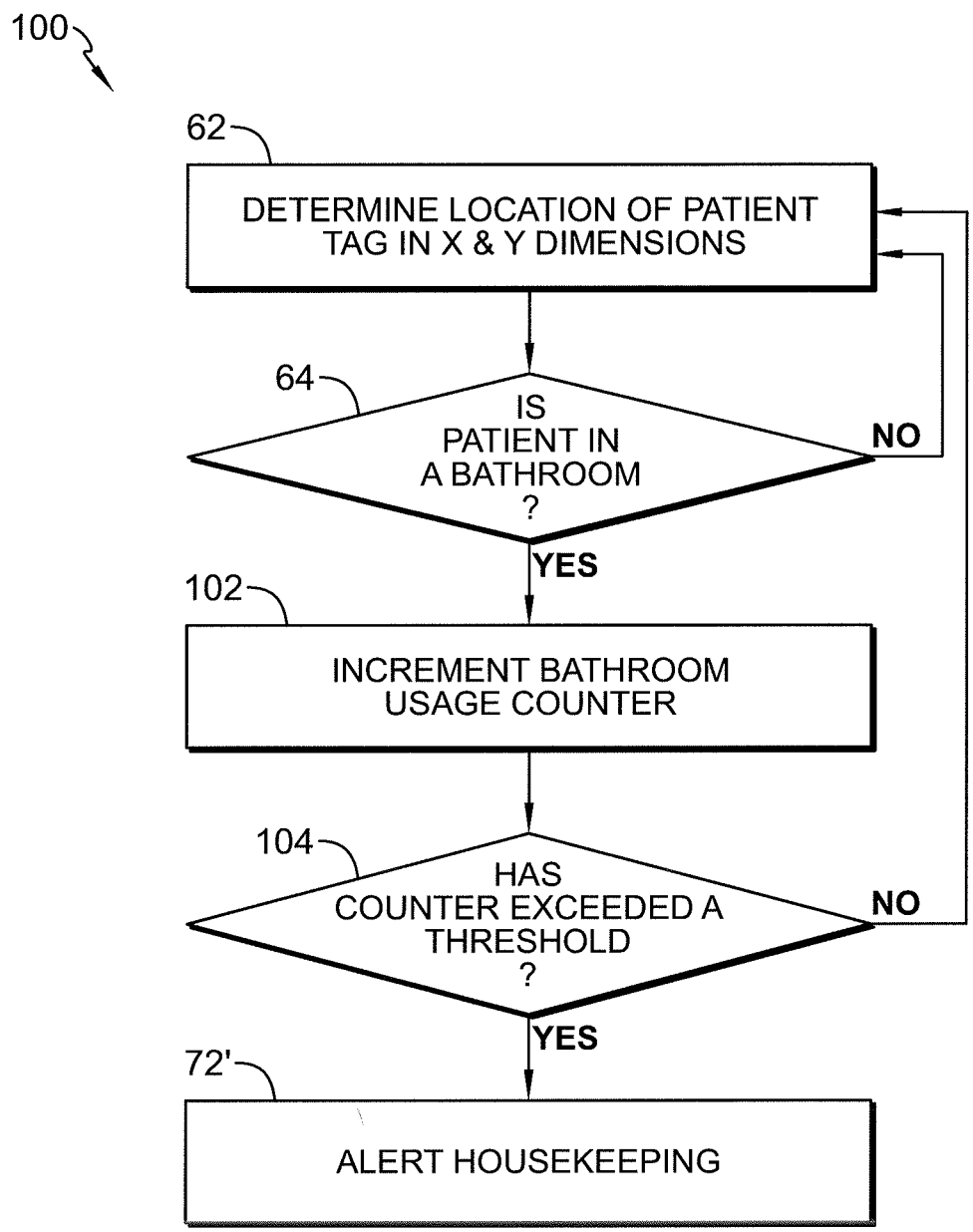
FIG. 6 is a block diagram showing a fourth flow chart that is representative of an algorithm to determine if patients have entered or used one of the bathrooms a threshold number of times to require a housekeeper to clean the bathroom.

According to the present disclosure and with reference to FIG. 6, system 10 is also configured, in some embodiments, with an algorithm 100 to notify housekeeping after a patient has used the bathroom 20a-20e of their patient room 18a-18e a set number of times so that the bathroom can be cleaned. The first two steps 62, 64 of algorithm 100 are the same as the first two steps 62, 64 of algorithm 60 described above and so these do not need to be repeated. If the patient is determined to be in the respective bathroom 20a-20e, algorithm 100 proceeds to step 102 to increment a bathroom usage counter. The bathroom usage counter of algorithm 100 is incremented at step 102 even if a caregiver accompanies the patient into the bathroom and even if door 42 remains opened. This is because algorithm 100 is monitoring the overall number of times the bathroom 20a-20e has been used since the last time the particular bathroom 20a-20e has been cleaned. After step 102, algorithm 104 determines whether the bathroom usage counter has exceeded a threshold. The bathroom usage threshold is three usages in some embodiments, for example, but a threshold greater than or less than three is within the scope of this disclosure at the discretion of the system designer.

If at step 104 the counter has not exceeded the threshold, algorithm 100 loops back to step 62 and proceeds from there. If at step 104 the counter has exceeded the threshold, then algorithm 100 proceeds to step 72' to alert housekeeping that the bathroom 20a-20e needs to be cleaned. Alerting housekeeping at step 72' includes sending a message to a housekeeping server 36 in some embodiments. The housekeeping server 36 may initiate an alert message to a mobile device carried by one or more housekeepers assigned to the particular patient room 18a-18e in some embodiments. Alternatively or additionally, the locating server 36 may initiate an alert message to a housekeeper's mobile device without involving any housekeeping server 36. In some embodiments, the indicator light or dome light outside the patient's room 18a-18e, is illuminated to alert caregivers or housekeepers in the vicinity of the light that the associated bathroom 20a-20e needs to be cleaned. Alert messages regarding the need for the bathroom 20a-20e to be cleaned may appear on other displays, such as a master nurse station computer 36, a status board display 36, one or more graphical room stations 36 of a nurse call system, and one or more staff stations 36 of a nurse call system in some embodiments. Audible alerts on the above-mentioned devices are also contemplated in connection with step 72' of algorithm 100.

In some embodiments, an alert may also be sent to a caregiver in connection with step 72' of algorithm 100 if an assigned patient uses the bathroom 20a-20e a threshold number of times within a given period of time, such as during the assigned caregiver's shift. Multiple uses of the bathroom 20a-20e by the patient within a given time frame may indicate a medical condition that requires the caregiver's attention. Thus, a timer may be employed in a variant of algorithm 100 for monitoring an amount of time that elapses for a threshold number of bathroom usages by the patient. The timer may be used to establish a time window (e.g., an 8-hour shift or 5-hours or some other time) within which a caregiver is notified if the patient uses the bathroom a threshold number of times (e.g., four times per shift or three times within a 5-hour window just to list a couple arbitrary examples). The threshold number of bathroom uses for caregiver notification may be a different number than the threshold number of uses for housekeeper notification according to the present disclosure.

System 10 also monitors the whereabouts of housekeepers according to the present disclosure by monitoring the location of tags 12 worn by the housekeepers. Thus, if a housekeeper enters one or more of bathroom 20a-20e for which a housekeeping alert has been sent in connection with step 72' of algorithm 100, then it is assumed that the housekeeper is cleaning the bathroom and the bathroom usage counter associated with step 102 of algorithm 100 is reset back to zero. It is also possible that a housekeeper may clean one or more of bathrooms 20a-20e, such as on a regular cleaning schedule, prior to the bathroom usage counter exceeding the threshold. Under that scenario, the bathroom usage counter associated with step 102 of algorithm is also reset back to zero since the bathroom has been cleaned. In some embodiments, an alert to housekeeping is sent in response to the bathroom usage counter equaling the threshold rather than exceeding a threshold (e.g., the threshold condition is equal to four bathroom uses, rather than checking for the next bathroom usage exceeding a threshold of three). Step 104 is considered to be representative of both of these scenarios. The bathroom usage counter for housekeeping notification is not reset in response to a caregiver entering the bathroom 20a-20e under the assumption that the caregiver is assisting the patient and is not cleaning the bathroom 20a-20e. As was the case with algorithms 60, 80, 90 described above, steps of algorithm 100 may be performed on any one or more of computers 30, 32, 36.

System 10 may be configured to run only one of algorithms 60, 80, 90, 100 but not the others. Alternatively, system 10 may be configured to run two of algorithms 60, 80, 90, 100 but not the other two. Further alternatively, system 10 may be configured to run three of algorithms 60, 80, 90, 100 but not the other one. Still further alternatively, system 10 may be configured to run all four of algorithms 60, 80, 90, 100. The algorithms 60, 80, 90, 100 may be run in parallel or may be run serially, one after the other, and then the serial sequence is repeated. In each of algorithms 60, 80, 90, 100 the steps subsequent to step 64 are not run unless one of tags 14 is first determined to be in one of bathrooms 20a-20e at step 64. Thus, the steps after step 64 of algorithms 60, 80, 90, 100 are run only for those tags 14 that are determined to be in bathrooms 20a-20e and, in some embodiments in the case of algorithms 60, 80, 90, upon the condition that a caregiver is not in the corresponding bathroom 20a-20e with the respective patient and/or upon the condition that the corresponding bathroom door 42 is closed as sensed by the associated sensor 40. By limiting the conditions upon which algorithms 60, 80, 90, 100 proceed to the respective steps after step 64, computational power of the computers 30, 32, 36 running some or all of algorithms 60, 80, 90, 100 is conserved thereby allowing computers to operate more efficiently and to complete other programmed tasks more quickly. Thus, limiting the conditions upon which algorithms 60, 80, 90, 100 proceed to the respective steps after step 64 minimizes the chances that computers 30, 32, 36 become overburdened which would have a tendency to slow down the overall operational efficiency of system 10.

If a caregiver alert or notification is sent to one or more caregivers in connection with algorithms 60, 80, 90, 100 or if a housekeeping alert or notification is sent to one or more housekeepers in connection with algorithm 100, it is contemplated by this disclosure that, in some embodiments, the alert is cleared from system 10 automatically in response to the one or more caregivers or housekeepers, as the case may be, being located in the respective bathroom 20a-20e from which the alert originated. In some embodiments, a caregiver or housekeeper is required to provide an input at a computer device 36 in order to clear the alert after the patient has received the necessary attention or after the bathroom has been cleaned, as the case may be. For example, caregivers and housekeepers may use graphical room stations 36 of a nurse call system that are located in rooms 18a-18e to clear the associated alerts in some embodiments. Alternatively or additionally, inputs to clear the alerts in system 10 may be input on the mobile devices of caregivers and housekeepers after the patient has received the necessary attention or after the bathroom has been cleaned, as the case may be.

In some embodiments, an administration screen is provided at the locating server 36, for example, to permit a system administrator to set the various thresholds and parameters of algorithms 60, 80, 90, 100. For example, the Z-dimension threshold and/or time threshold of algorithm 60, the time delay and/or drop threshold of algorithm 80, the time threshold of algorithm 90, and/or the bathroom usage threshold of algorithm 100 may be selectable, such as from associated drop down menus, or may be otherwise settable by the system administrator using the administration screen. These thresholds and parameters may therefore have different values for different rooms and patients, if desired.

Alternatively or additionally, some or all of the thresholds and parameters just mentioned may be established based on information provided to the locating server 36 from other computers 36 of system 10. For example, if a particular patient is designated as a falls risk in an EMR server 36, then the locating server 36 may set a default time threshold in algorithm 60 for the falls risk patient that is less than a default time threshold for a patient that is not designated as a falls risk. In a similar manner, if a patient has a highly contagious medical condition, such as being diagnosed with Methicillin-resistant *Staphylococcus aureus* (MRSA) bacteria, then the bathroom usage threshold may be set to a default value by the locating server 36 that is less than the default value set for patients that do not have a MRSA diagnosis.

Although this disclosure refers to specific embodiments, it will be understood by those skilled in the art that various changes in form and detail may be made without departing from the subject matter set forth in the accompanying claims.

The invention claimed is:

1. A bathroom monitoring system comprising:
a computer,
a plurality of transceivers mounted at fixed locations throughout the healthcare facility and communicatively coupled to the computer,
a patient identification (ID) tag that is worn by a patient, the patient ID tag having a first tag transceiver configured to communicate with the plurality of transceivers, and
a housekeeper identification (ID) tag that is worn by a housekeeper, the housekeeper ID tag having a second tag transceiver configured to communicate with the plurality of transceivers,
wherein the plurality of transceivers and the computer cooperate to form a high-accuracy locating system that is operable to determine a location of the patient ID tag and the housekeeper ID tag within one foot or less of the patient ID tag's and housekeeper ID tag's actual location, respectively,
wherein the high-accuracy locating system monitors a location of the patient via signals from the first tag transceiver to determine whether a patient has entered a bathroom, the computer incrementing a counter to count a number of times that the patient enters the bathroom and initiating an alert to the housekeeper if the number of times that the patient enters the bathroom exceeds a predetermined threshold, the high-accuracy location system monitoring a location of the housekeeper via signals from the second tag transceiver, the computer resetting the counter to zero in response to the housekeeper entering the bathroom.

2. The bathroom monitoring system of claim 1, wherein the predetermined threshold is three times.

3. The bathroom monitoring system of claim 1, wherein the computer tracks an amount of time that the patient has been in the bathroom, compares the amount of time to a predetermined time, and initiates an alert to a caregiver if the amount of time exceeds the predetermined time.

4. The bathroom monitoring system of claim 1, wherein the computer of the high-accuracy locating system determines that the patient has fallen based on an elevation of the patient ID tag relative to a reference plane violating a height threshold.

5. The bathroom monitoring system of claim 4, wherein the height threshold is defined by a height of a seat of a toilet in the bathroom.

6. The bathroom monitoring system of claim 4, wherein the reference plane is defined as a substantially horizontal plane that passes through at least two transceivers mounted at a substantially equivalent distance above a floor of the bathroom.

7. The bathroom monitoring system of claim 4, wherein the reference plane is defined as a substantially horizontal plane that passes through at least two transceivers mounted at a substantially equivalent distance below a floor of the bathroom.

8. The bathroom monitoring system of claim 4, wherein, if the computer determines that the patient has fallen, the computer initiates an alert to a nurse's station or to a wireless communication device of a caregiver.

9. The bathroom monitoring system of claim 1, wherein the computer of the high-accuracy locating system determines that the patient has fallen based on an elevation of the patient ID tag relative to a reference plane violating a height threshold for a predetermined amount of time.

10. The bathroom monitoring system of claim 1, wherein the computer tracks a rate of change in an elevation of the patient ID tag to determine whether the patient has fallen.

11. The bathroom monitoring system of claim 10, wherein the computer initiates an alert to a nurse's station or to a wireless communication device of a caregiver if the computer determines that the patient has fallen.

12. The bathroom monitoring system of claim 1, wherein the computer initiates an alert to a nurse's station or to a wireless communication device of a caregiver if the number of times that the patient uses or enters the bathroom exceeds a predetermined threshold within a predetermined period of time.

13. The bathroom monitoring system of claim 1, further comprising a caregiver identification tag that includes a caregiver transceiver to communicate with the high-accuracy locating system, the computer incrementing the counter in response to the caregiver entering the bathroom.

14. The bathroom monitoring system of claim 1, wherein the first and second tag transceivers communicate with the plurality of transceivers via ultra-wideband (UWB) signals.

15. The bathroom monitoring system of claim 1, wherein the locations of the patient ID tag and the housekeeper ID tag are determined by the computer using two way ranging and time difference of arrival (TDOA) techniques.

16. The bathroom monitoring system of claim 1, wherein the computer uses signals from only a subset of the plurality of transceivers to determine the locations of the patient ID tag and the housekeeper ID tag, the subset being determined based on signal strength of signals from the first tag transceiver and the second tag transceiver to the plurality of transceivers.

17. The bathroom monitoring system of claim 16, wherein the subset comprises at least three transceivers from the plurality of transceivers having highest signal strength values as compared to others of the plurality of transceivers.

* * * * *